(12) United States Patent
Watson et al.

(10) Patent No.: US 6,329,657 B1
(45) Date of Patent: Dec. 11, 2001

(54) COINCIDENCE TRANSMISSION SOURCE

(75) Inventors: Charles C. Watson; Ronald Nutt, both of Knoxville; J. Clifton Moyers, Oak Ridge; Michael E. Casey; William F. Jones, both of Knoxville, all of TN (US)

(73) Assignee: CTI Pet Systems, Inc., Knoxville, TN (US)

( * ) Notice: Subject to any disclaimer, the term of this patent is extended or adjusted under 35 U.S.C. 154(b) by 0 days.

(21) Appl. No.: 09/070,951

(22) Filed: May 1, 1998

(51) Int. Cl.[7] .................................................. G01T 1/163
(52) U.S. Cl. .............................. 250/363.04; 250/363.03; 250/363.09
(58) Field of Search ...................... 250/363.03, 363.04, 250/363.09

(56) References Cited

U.S. PATENT DOCUMENTS

| 4,743,764 | 5/1988 | Casey et al. ........................................ |
| 5,773,829 | * 6/1998 | Iwanczyk et al. .................... 250/367 |

FOREIGN PATENT DOCUMENTS

| 59-99377 (A) | * 6/1984 | (JP) ................................ 250/363.09 |
| 59-180477 (A) | * 10/1984 | (JP) ................................ 250/363.04 |
| 61-235782 (A) | * 10/1986 | (JP) ................................ 250/363.04 |

OTHER PUBLICATIONS

S.R. Cherry, et al.: "Optical Fiber Readout of Scintillator Arrays using a Multi–Channel PMT: A High Resolution PET Detector for Animal Imaging", IEEE Transactions on Nuclear Science, vol. 43, No. 3, 1932–1937 (Jun., 1996).

J.A. McIntyre, et al.: "Construction of a Positron Emission Tomograph with 2.4 mm Detectors", IEEE Transactions on Nuclear Science, vol. 33, No. 1, 425–427 (Feb., 1986).

C. J. Thompson, N. T. Ranger, and A. C. Evans, "Simultaneous Transmission and Emission Scans in Positron Emission Tomography." Presented at the IEEE Nuclear Science Symposium, Orland, Florida, seven pages, Nov. 1988.*

* cited by examiner

*Primary Examiner*—Constantine Hannaher
(74) *Attorney, Agent, or Firm*—Pitts & Brittian, P.C.

(57) ABSTRACT

A coincidence transmission source serves to detect coincident activity from a radiation source. The coincidence transmission source includes a detector dedicated to collecting attenuation data. A collimated radiation source and a detector are positioned with respect to a tomography device such that only a selected strip of the imaging detector of the tomograph is illuminated such that events unrelated to the attenuation are eliminated. The coincidence transmission source includes a collimator in which is disposed a radiation source. An opening is defined by the collimator for exposing a selected portion of the imaging detectors of the tomograph device. Positioned behind the radiation source, relative to the imaging detectors, is the dedicated attenuation detector. The attenuation detector and collimator are designed to illuminate only a strip of the imaging detector, thereby eliminating events not of interest in the attenuation measurement. In a dual head tomograph device, one coincidence transmission source of the present invention is disposed opposite each bank of imaging detectors. The sources and the associated collimators are positioned to the side of each head at a slight angle relative to the respective head. The sources and detectors are fixed relative to the imaging heads. In order to obtain full coverage of the field of view (FOV) in the same manner as for an emission scan, the heads and sources are rotated about the center of the camera.

20 Claims, 5 Drawing Sheets

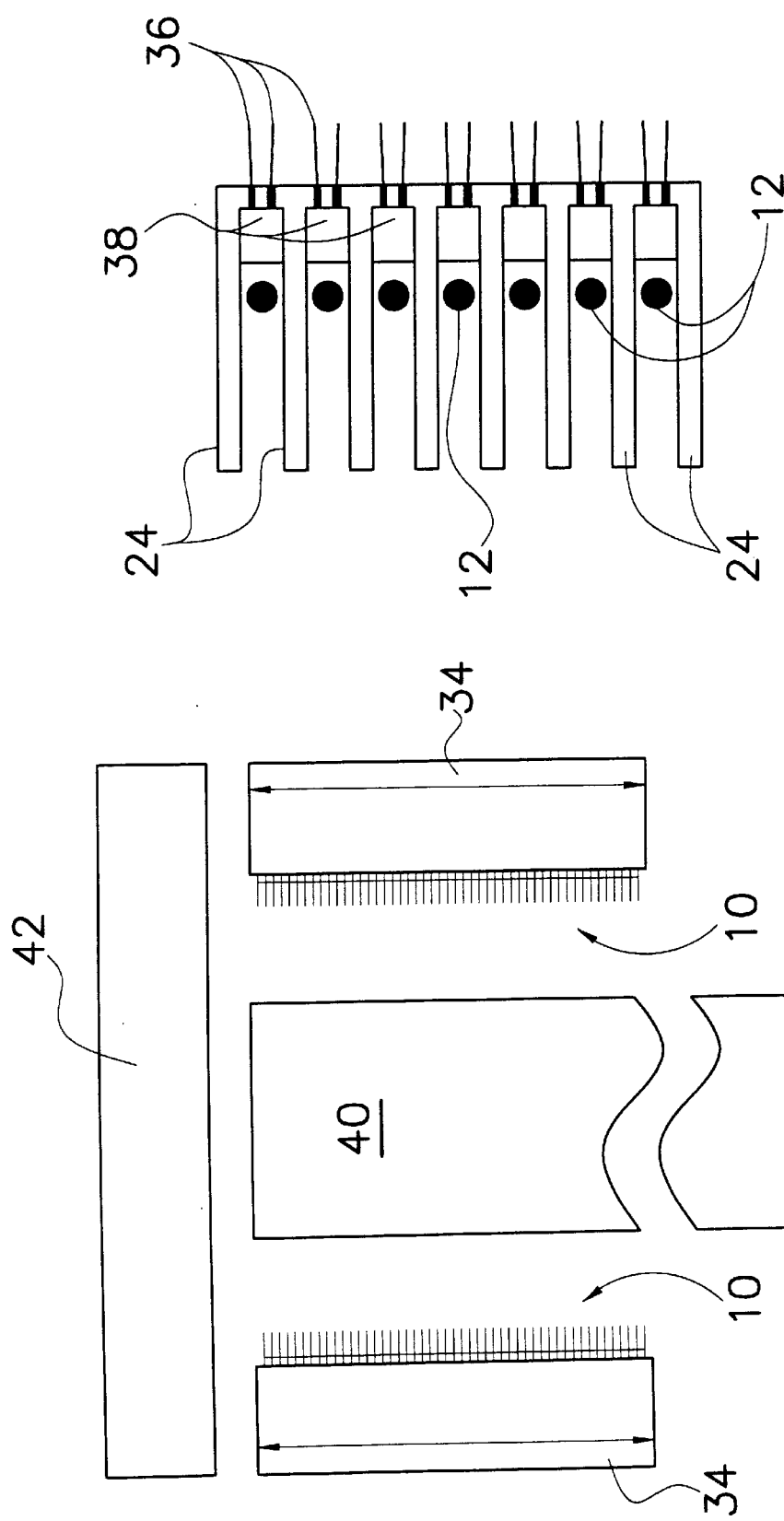

COINCIDENCE TRANSMISSION SOURCE

TECHNICAL FIELD

This invention relates to the field of tomography. More specifically, the present invention relates to a method of measuring the attenuation associated with detecting coincidences using a collimated source and a dedicated detector for improved measurement sensitivity.

BACKGROUND ART

Positron Emission Tomography (PET) has gained significant popularity in nuclear medicine because of the ability to non-invasively study physiological processes within the body. Applications employing the PET technology for its sensitivity and accuracy include those in the fields of oncology, cardiology and neurology.

Using compounds such as $^{11}$C-labeled glucose, $^{18}$F-labeled glucose, $^{13}$N-labeled ammonia and $^{15}$O-labeled water, PET can be used to study such physiological phenomena as blood flow, tissue viability, and in vivo brain neuron activity. Positrons emitted by these neutron deficient compounds interact with free electrons in the body area of interest, resulting in the annihilation of the positron. This annihilation yields the simultaneous emission of a pair of photons (gamma rays) approximately 180° (angular) apart. A compound having the desired physiological effect is administered to the patient, and the radiation resulting from annihilation is detected by a PET tomograph. After acquiring these annihilation "event pairs" for a period of time, the isotope distribution in a cross section of the body can be reconstructed.

PET data acquisition occurs by detection of both photons emitted from the annihilation of the positron in a coincidence scheme. Due to the approximate 180° angle of departure from the annihilation site, the location of the two detectors registering the "event" define a chord passing through the location of the annihilation. By histogramming these lines of response (the chords), a "sinogram" is produced that may be used by a process of back-projection to produce a three dimensional image of the activity. Detection of these lines of activity is performed by a coincidence detection scheme. A valid event line is registered if both photons of an annihilation are detected within a coincidence window of time. Coincidence detection methods ensure (disregarding other second-order effects) that an event line is histogrammed only if both photons originate from the same positron annihilation.

In the traditional (2-D) acquisition of a modern PET tomograph, a collimator (usually tungsten) known as a septa is placed between the object within the field-of-view and the discrete axial rings of detectors. This septa limits the axial angle at which a gamma ray can impinge on a detector, typically limiting the number of axial rings of detectors that a given detector in a specific ring can form a coincidence with to a few rings toward the front of the tomograph from the given detector's ring, the same ring that the detector is within, and a few rings toward the rear of the tomograph from the given detector's ring.

Attenuation was first measured in PET by using a ring of positron emitting isotope surrounding the object to be measured. In this technique, the ratio between a transmission scan and a blank scan form the attenuation. The blank is measured by simply measuring the rate that gamma rays from positrons are detected by the detection system when no attenuating media is present. In the original scanners as described above as having septa, the septa are provided for collimating the gamma rays in an axial direction, but the rings allow for no transaxial collimation. The lack of collimation allow the acceptance of scattered events into the transmission measurement, resulting in an underestimate of the attenuation. To improve the transmission measurement, systems use rotating rod sources. These sources are disposed in parallel fashion to the axis of the scanner and are collimated in the axial direction by the septa. In the transaxial direction, the collimation may be provided electronically since the position of the source is known. However, the activity in the rod must be the same as that activity in the earlier ring source to provide the same count rate. With modern block detectors, the dead-time of the near block limits the activity in the rod.

A more recent advancement in PET acquisition is 3-D, in which the septa are removed, which allows a given detector to be in coincidence with detectors from all other detector rings. With the advent of three-dimensional reconstruction techniques, greater sensitivity to emission counts is possible if the septa are removed. As the septa represent a significant cost, there is also an economic incentive to exclude them from the system. However, with the absence of septa, the problems of both detector dead-time and scatter are magnified.

Since the position of a source with respect to the detector system can be known, there is no need to detect coincidences, thereby allowing the use of a source that emits single gamma rays. Only one detector—the detector on the far side of the system—is needed to make the transmission or blank measurements. Without the counting losses due to the dead-time of the near detector, the activity of the source may be increased resulting in an increase in count-rate and thus a better quality measurement. However, without axial collimation, the scatter included in the transmission scan causes an underestimate of the attenuation measurement. To decrease the possibility of scatter, the gamma rays from the source can be collimated with lead or tungsten to form a beam that illuminates only a narrow plane of detectors. Other gamma rays that would only contribute to background are eliminated. Since the directionality of single gamma rays cannot be determined, only a single point of activity illuminating a detector bank can be used. This requires increased levels of activity to meet the count-rate needed for an adequate quality measurement. Also, the scanning protocol is more efficient if the transmission measurement is performed after the patient has been injected with radioactivity. Even though a different isotope such as $^{137}$Cs which emits gamma rays with an energy of 662 keV can be used for the transmission scan, there is a significant difficulty in distinguishing the transmission events from the emission events.

Another tomographic diagnostic system that is similar to PET is known as single photon emission computed tomography (SPECT). The distinction is that in SPECT, only a single photon from a nuclear decay within the patient is detected. Also, the line of response traveled by the photon is determined exclusively by detector collimation in SPECT, as opposed to the coincident detection of two collinear photons as in PET.

In computed axial tomography (CAT, or now also referred to as CT), an external x-ray source is caused to be passed around a patient. Detectors around the patient then respond to x-ray transmission through the patient to produce an image of an area of study. Unlike PET and SPECT, which are emission tomography techniques because they rely on detecting radiation emitted from the patient, CT is a transmission tomography technique which utilizes only a radiation source external to the patient.

The details of carrying out a PET study are given in numerous publications. Typically, the following references provide a background for PET. These are incorporated herein by reference for any of their teachings.

1. M. E. Phelps, et al.: "Positron Emission Tomography and Audiography", Raven Press, 1986;
2. R. D. Evans: "The Atomic Nucleus", Kreiger, 1955;
3. J. C. Moyers: "A High Performance Detector Electronics System for Positron Emission Tomography", Masters Thesis, University of Tennessee, Knoxville, Tenn., 1990;
4. U.S. Pat. No. 4,743,764 issued to M. E. Casey, et al, on May 10, 1988;
5. R. A. DeKemp, et al.: "Attenuation Correction in PET Using Single Photon Transmission Measurement", Med. Phys., vol. 21, 771–8, 1994;
6. S. R. Cherry, et al.: "3-D PET Using a Conventional Multislice Tomograph Without Septa", Jl. C. A. T., 15(4) 655–668.
7. J. S. Karp, et al.: "Singles Transmission in Volume-Imaging PET With a $^{137}$Cs Source", Phys. Med. Biol. Vol. 40, 929–944 (1995).
8. S. K. Yu, et al.: "Single-Photon Transmission Measurements in Positron Tomography Using $^{137}$Cs", Phys. Med. Biol. Vol. 40, 1255–1266 (1995).
9. G. F. Knoll: *Radiation Detection and Measurement*, John Wiley & Sons (1989).
10. S. R. Cherry, et al.: "Optical Fiber Readout of Scintilator Arrays using a Multi-Channel PMT: A High Resolution PET Detector for Animal Imaging", IEEE Transactions on Nuclear Science, Vol. 43, No. 3, 1932–1937 (June, 1996).
11. J. A. McIntyre, et al.: "Construction of a Positron Emission Tomograph with 2.4 mm Detector", IEEE Transactions on Nuclear Science, Vol. 33, No. 1, 425–427 (February, 1986).

Both SPECT and CAT (or CT) systems are also well known to persons skilled in the art.

In order to achieve maximal quantitative measurement accuracy in tomography applications, an attenuation correction must be applied to the collected emission data. In a PET system, for example, this attenuation is dependent on both the total distance the two gamma rays must travel before striking the detector, and the density of the attenuating media in the path of travel. Depending on the location of the line of response within the patient's body, large variations in attenuating media cross section and density have to be traversed. If not corrected for, this attenuation causes unwanted spatial variations in the images that degrade the desired accuracy. As an example, for a cardiac study the attenuation is highest in the line of responses (LORs) passing through the width of the torso and arms, and attenuation is lowest in the LORs passing through from the front to the back of the chest.

Typically, the attenuation correction data in PET systems is produced by either: shape fitting and linear calculations using known attenuation constants, these being applicable to symmetric well-defined shapes such as the head and torso below the thorax (calculated attenuation); or through the measurement of the annihilation photon path's attenuation using a separate transmission scan (measured attenuation). The use of calculated attenuation correction, which introduces no statistical noise into the emission data, can be automated for simple geometries such as the head, and is the most prominent method used for brain studies. However, complexities in the attenuation media geometry within the chest have prevented the application of calculated attenuation from being practical for studies within this region of the body. Accordingly, transmission scanning has been utilized.

The total attenuation of a beam along a LOR through an object is equal to the attenuation that occurs for the two photons from an annihilation. Thus, the emission attenuation along the path can be measured by placing a source of gamma rays on the LOR outside of the body and measuring attenuation through the body along this line. It has been the practice to accomplish this attenuation measurement by placing a cylindrical positron emitter "sheet" within the PET tomograph's field of view (FOV) but outside of the region (the object) to be measured. The ratio of an already acquired blank scan (no object in the FOV) to the acquired transmission scan is calculated. These data represent the desired measured attenuation factors, which may vary spatially. These data are then applied to the emission data after a transmission scan of the object to correct for the spatial variations in attenuation.

There are two types of transmitter source units conventionally utilized in PET transmission scan data collection, both of which form a "sheet" of activity to surround the patient. One involves the placement of rings of activity aligned with detector rings around the inner face of the septa. The second type utilizes the rotation of one or more axially-oriented rods of activity in a circular path just inside the inner face of the septa.

The first of these two emitter systems (the ring source method) significantly reduces the sensitivity of the tomograph due to the close source-proximity dead time effects of the source activity on all of the detectors. Further, removal of this assembly is either performed manually by facility personnel or by a complex automated mechanical assembly. Large, cumbersome, out of the FOV shielding is required for storage of the automated source when not in use, adding to the depth of the tomograph tunnel and, thus increasing incidence of patient claustrophobia. The second type of emitter, using rotating source(s) suffers from the above-mentioned problems and also, due to the shielding requirements, reduces the patient tunnel diameter, further increasing patient claustrophobia symptoms.

Both of the above automated source transportation methods suffer from high mechanical component cost and from low sensitivity. Due to the dead-time-induced reduction in tomograph sensitivity, lengthy acquisitions are required in order to achieve usable low noise transmission scan data.

In order to reduce costs in scintillator detector applications, multiplexing techniques based on the use of fiber optics are advantageous. Those disclosures made by Cherry, et al. (Cherry), and McIntyre, et al. (Mcintyre), teach the use of fiber optics connected between the imaging detectors and multichannel photomultipliers (PMT's). Cherry discloses the use of a multi-channel PMT in association with an 8×8 array of bismuth germanate (BGO) crystals. As discussed by Cherry, a charge division readout board is used to convert the 64 signals into four position sensitive signals which determine the crystal interaction. In the earlier McIntyre article, the authors disclose the use of fiber optics coupled between the detectors and a number of multi-channel PMT's. Specifically, McIntyre teaches the use of 288 PMT's in association with 8,192 detectors, for reducing the number of required PMT's by a factor of about 28.4.

In the McIntyre embodiment, eight detector rings are each divided into four quadrants. Each ring is comprised of sixteen concentric rings. The respective quadrants for the eight detector rings are grouped together for a total of 256 detectors per quadrant group. Sixteen "coarse" fiber sets connect sixteen PMT's to the 256 detectors, with sixteen detectors in one ring quadrant connected to one PMT. Similarly, sixteen "fine" fiber sets connect sixteen PMT's to the 256 detectors, with corresponding detectors in each ring quadrant of a quadrant group being connected to one PMT. One PMT is connected to each ring quadrant. Thus, a total of 32 PMT's are required for determining the particular detector "Θ" address within a quadrant. Similarly, 32 PMT's are required to determine the "r" address, corresponding to which of the concentric rings in a particular ring the detector is disposed. Finally, eight PMT's are required to determine which ring quadrant the detector is disposed. Thus, a total of 72 PMT's are required for each quadrant for a total of 288 PMT's in association with 8,192 detectors.

Therefore, it is an object of the present invention to provide a system for detecting coincident activity from a point source.

Another object of the present invention is to provide such a system which includes a detector dedicated to collecting attenuation data.

Yet another object of the present invention is to provide a system for detecting coincident activity while illuminating only a strip of the imaging detector in order to eliminate events not of interest in the attenuation measurement.

A further object of the present invention is to provide a collimated point source and dedicated detector whereby only a selected strip of the imaging detector is illuminated such that events unrelated to the attenuation are eliminated.

Still another object of the present invention is to provide an arrangement whereby gamma radiation detected by dedicated detectors is transmitted to a plurality of PMT's such that an address of each gamma radiation detector is readily determined and such that the total required number of PMT's is reduced relative to conventional devices.

DISCLOSURE OF THE INVENTION

Other objects and advantages will be accomplished by the present invention which serves to detect coincident activity from a collimated point source. The present invention includes a detector dedicated to collecting attenuation data. The collimated point source and dedicated detector are positioned with respect to the tomography device such that only a selected strip of the imaging detector is illuminated such that events unrelated to the attenuation are eliminated.

The source of the present invention includes a collimator in which is disposed a point source. An opening is defined by the collimator for exposing a selected portion of the imaging detectors of the tomograph device. Positioned behind the point source, relative to the imaging detectors, is an attenuation detector dedicated to collecting attenuation data. Because the attenuation detector is dedicated to the attenuation measurement, the requirements for the attenuation detector are different from those for the imaging detector. For instance, it is not required that the attenuation detector be able to accurately determine the energy or spatial position of events within the detector, as is necessary for standard imaging detectors. It is therefore possible to design such an attenuation detector with much less dead time, and much higher count rate performance, than a standard imaging detector. The improved count rate performance of the attenuation detector enables significant reduction of statistical noise in the attenuation correction measurement. The attenuation detector and collimator are designed to illuminate only a strip of the imaging detector, and the corresponding aperture of the attenuation detector, thereby eliminating events not of interest in the attenuation measurement. This also reduces dead time of the system and improves the count rate performance for events of interest.

A source of the present invention is disposed opposite each bank of imaging detectors of a dual head camera. Each source contains four point sources arranged along the axial extent. The sources and the associated collimators are positioned to the side of each head at a slight angle relative to the respective head. The sources and detectors are fixed relative to the imaging heads. In order to obtain full coverage of the field of view (FOV) in the same manner as for an emission scan, the heads and sources are rotated about the center of the camera.

The present invention further provides an arrangement of fiber optics interconnected between a plurality of dedicated gamma radiation detectors and a lesser number of photomultiplier tubes. The gamma radiation detectors are each provided for dedicated detection of 511 keV gamma radiation from one of a plurality of point sources disposed in a collimator. The arrangement of fiber optics is designed such that the address of a particular gamma radiation detector is readily discernable while minimizing the number of PMT's required to process data accumulated by the gamma radiation detectors.

BRIEF DESCRIPTION OF THE DRAWINGS

The above mentioned features of the invention will become more clearly understood from the following detailed description of the invention read together with the drawings in which:

FIG. 5 illustrates a top plan view of a dual head tomograph incorporating two banks of collimated point sources made in accordance with several features of the present invention;

FIG. 6 illustrates an enlarged portion of a collimator showing an arrangement between a plurality of point sources, a similar plurality of dedicated gamma radiation detectors, and corresponding pairs of fiber optic cables.

BEST MODE FOR CARRYING OUT THE INVENTION

Figure 1:
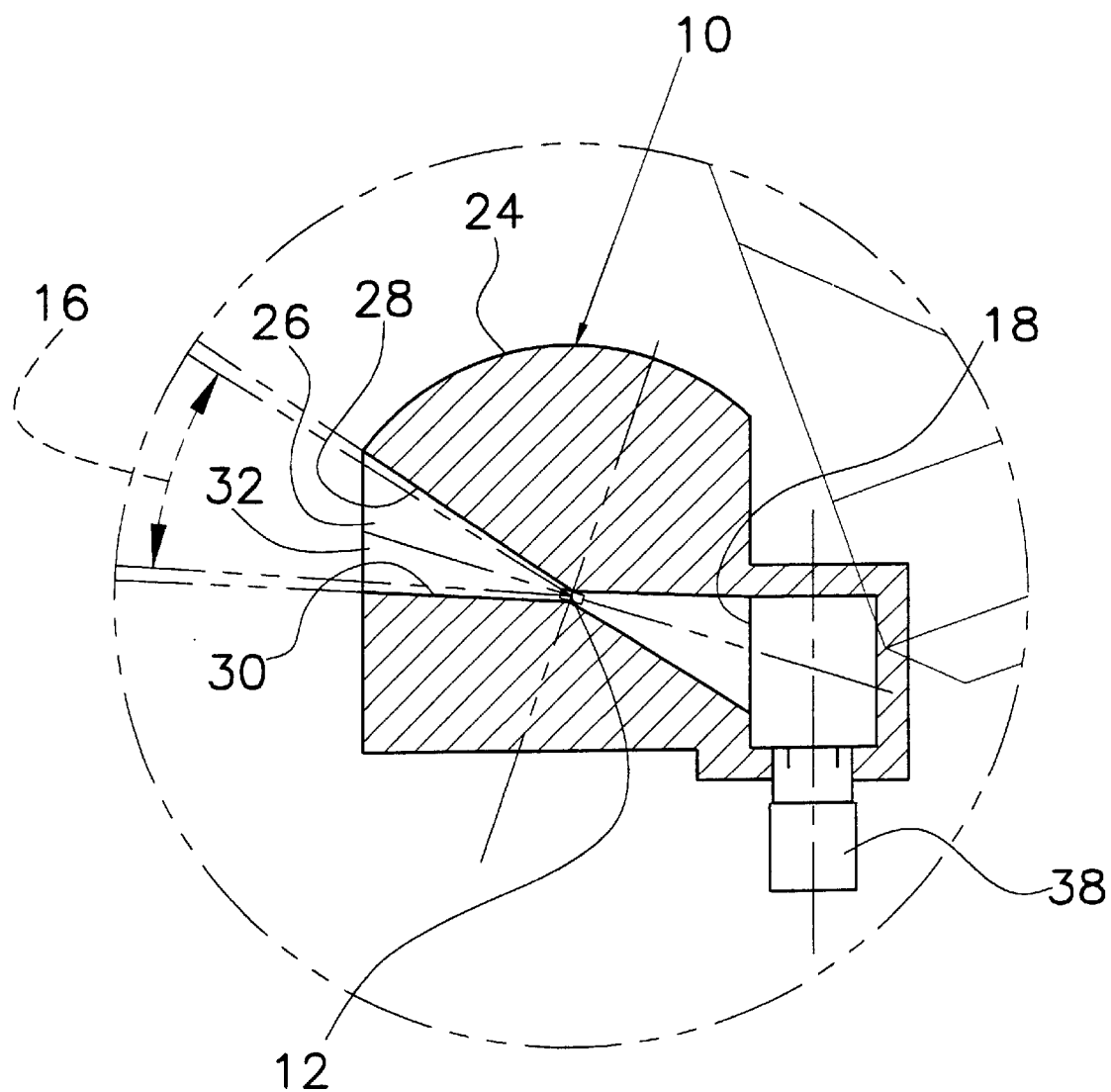
FIG. 1 is an end elevation view, in section, of the coincidence transmission source constructed in accordance with several features of the present invention showing a collimated point source and a dedicated detector.

A coincidence transmission source incorporating various features of the present invention is illustrated generally at 10 in the figures. The coincidence transmission source, or device 10, is designed for collimating and detecting coincident activity from a source 12 of radiation such as the illustrated point source 12. Moreover, the device 10 of the present invention includes a detector 18 dedicated to collecting attenuation data. The collimated point source 12 and dedicated attenuation detector 18 are positioned with respect to the tomography device 22 such that only a selected strip of the imaging detector 14 is illuminated such that events unrelated to the attenuation are eliminated. The imaging detector 14 may be comprised of either a plurality of imaging detectors 14 or a single continuous imaging detector 14 having spatial positioning capabilities.

As will be discussed throughout, many variations of the present invention may be adapted to fit various conventional applications of tomography. For example, the device 10 of the present invention may be adapted to various conventions of PET, SPECT, and other tomography applications or combinations thereof. The radiation source 12 may define various configurations, as will be discussed below, as required. Further, the radiation source 12 may be maintained stationary with respect to either or both of the dedicated attenuation detector 18 and the imaging detector 14, or may be moved to various positions within the tomograph device for individually collecting attenuation data corresponding to more than one imaging detector 14. In the latter case, the path in which the radiation source 12 is moved may be in any conventional path, or any path yet to be employed.

The device 10 of the present invention includes a collimator 24 in which is disposed a point source 12. An opening 26 is defined by the collimator 24 for exposing a selected portion of the imaging detectors 14 of the tomograph device 22. To this extent, the opening 26 defines a top and a bottom shield wall 28,30, with the top shield wall 28 extending from the point source 12 toward the far detector 44 of the imaging detectors 14 opposite the device 10, and the bottom shield wall 30 extending toward the near detector 46 of the imaging detectors 14. Side shield walls 32 are defined to limit the width of the collimated radiation beam. Positioned behind the point source 12, relative to the imaging detectors 14, is an attenuation detector 18 dedicated to collecting attenuation data.

Because the attenuation detector 18 is dedicated to the attenuation measurement, the requirements for the attenuation detector 18 are different from those for the imaging detectors 14. The attenuation detector 18 of the preferred embodiment consists of a single crystal of dense, fast material such as Lutetium Oxyorthosilicate (LSO) coupled to a single photomultiplier 38. However, it will be understood that other scintillator materials may be used as the material of manufacture of the attenuation detector 18 as required. Because the attenuation detector 18 is provided only for detecting events from the point source 12, good energy resolution is not of great importance. Further, because the attenuation detector 18 is positioned proximate the point source 12, the attenuation detector 18 is selected to exhibit low dead-time losses. The attenuation detector 18 and collimator 24 are designed to illuminate only a strip of the imaging detector 14, thereby eliminating events not of interest in the attenuation measurement. As a result of the coincident measurement allowing for electronic collimation, attenuation measurements may be made in the presence of other radiation such as that from a pre-injected patient. Further, the electronic collimation allows for the use of multiple point sources 12, thereby reducing the activity requirements on a single source 12.

Figure 2:
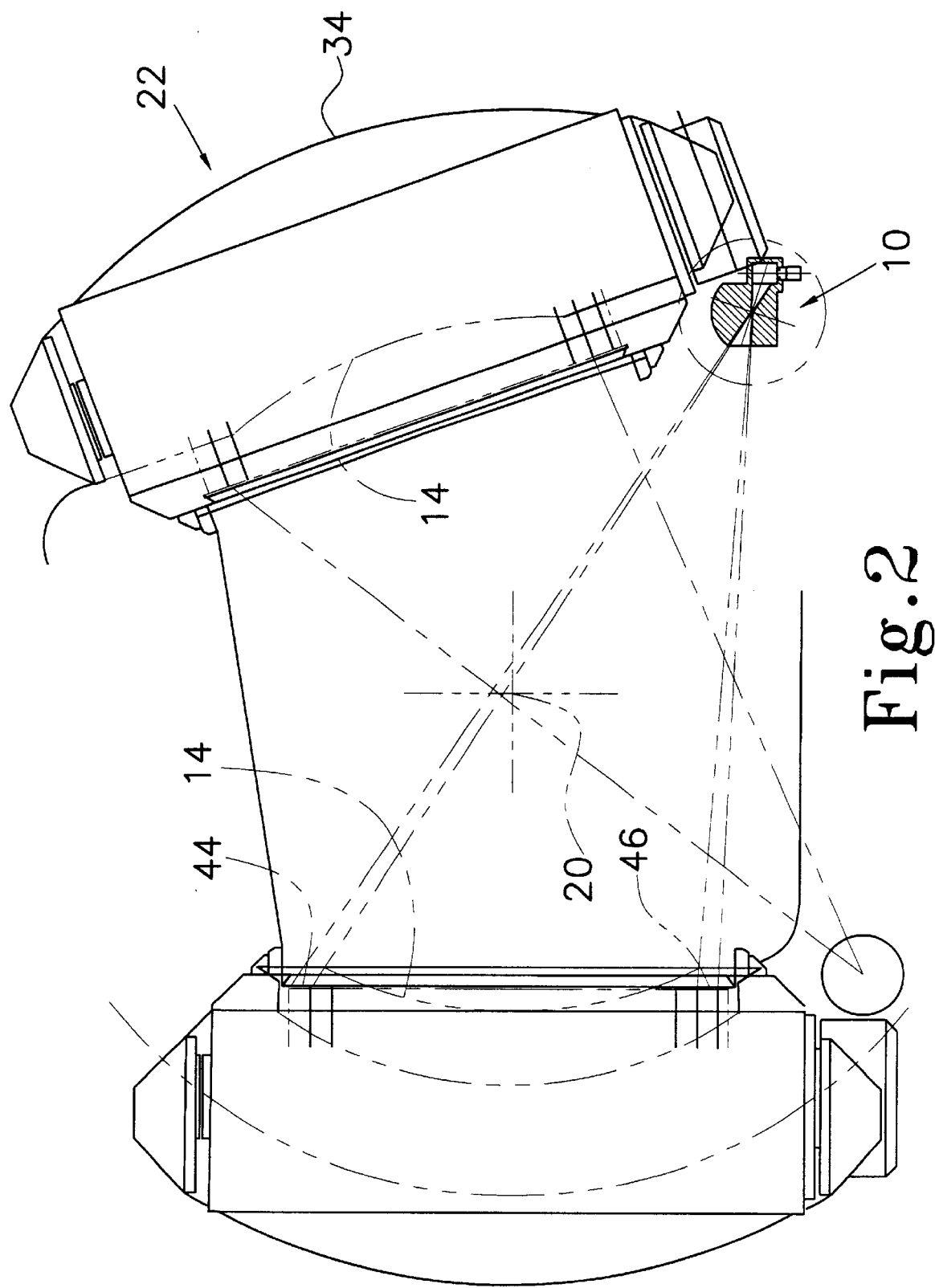
FIG. 2 illustrates an end elevation view, in section, of the coincidence transmission source of FIG. 1 showing the point source and detector positioned relative to a two head camera.

FIG. 2 illustrates a device 10 of the present invention disposed opposite each bank of imaging detectors 14 of a dual head camera 22. In the preferred embodiment, each device 10 contains four point sources 12 arranged along the axial extent. The sources 10 and the associated collimators 24 are positioned to the side of each head 34. Because it is preferred that the radiation beam from the point source 12 illuminate the center point 20 of the patient opening 35 (see also FIG. 3), each device 10 is positioned at a slight angle relative to the respective head. As illustrated, the sources 10 and detectors are fixed relative to the imaging heads 34. In order to obtain fill coverage of the FOV 16 in the same manner as for an emission scan, the heads and sources 10 are rotated about the center point 20.

Figure 3:
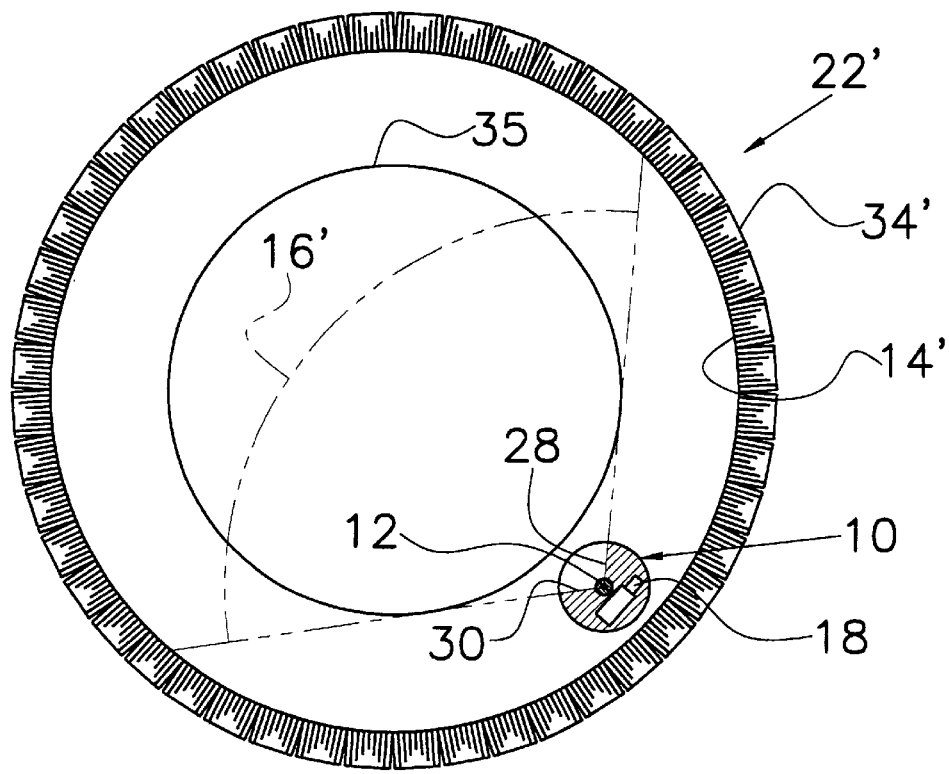
FIG. 3 illustrates an end elevation view, in section, of the coincidence transmission source of the present invention showing the point source and detector positioned within a fill ring detector.

As illustrated in FIG. 3, the device 10 of the present invention may also be used in association with a full-ring tomograph 22'. In this environment, the device 10 is disposed between the imaging detector ring 34' and the patient opening 35 so as not in interfere with the placement of the patient. In this embodiment, the device 10 is movable within the tomograph 22' in a conventional manner in order to collect attenuation data from each of the plurality of imaging detectors 14'.

Figure 4:
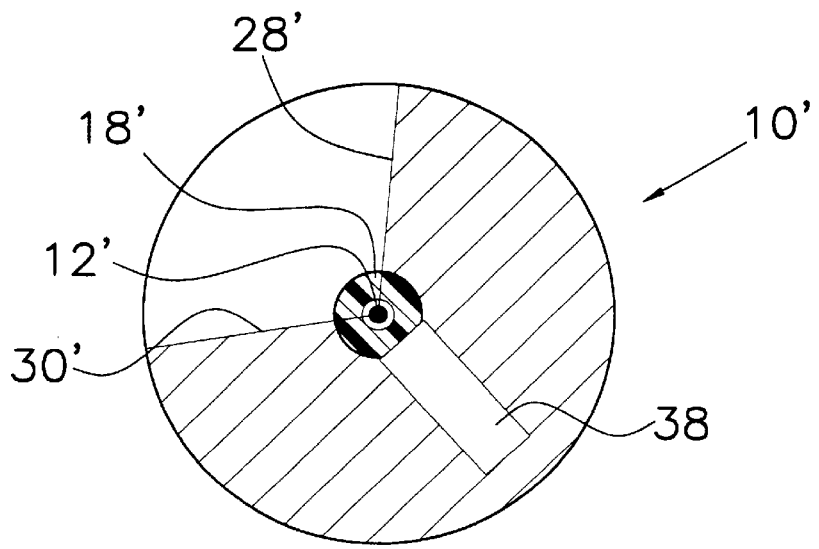
FIG. 4 illustrates an end elevation view, in section, of the coincidence transmission source showing the point source encapsulated within a scintillator.

FIG. 4 illustrates an alternate embodiment of the device 10' whereby the point source 12' is encased within a plastic scintillator 18' provided for detecting beta rays emitted from the point source 12'. A photomultiplier 38 is disposed behind the point source 12' relative to the viewable imaging detectors 14'. It will be seen by those skilled in the art that other constructions of the present invention may be accomplished whereby an attenuation detector 18 is dedicated solely to the collection of attenuation data from an attenuation point source 12.

FIG. 5 illustrates the top plan view of a dual head tomograph 22 device having two banks of collimated point sources 12 positioned in reference to a patient bed 40 and a gantry 42. FIG. 6 is an enlarged view of a portion of one bank of the collimated point sources 12. One point source 12 is disposed between successive pairs of collimators 24 and immediately in front of one dedicated gamma radiation detector 18. However, it will be understood by those skilled in the art that a single source 12 of radiation may define a rod-shaped configuration and extend behind or through the collimators 24 and thus successfully serve as the plurality of point sources 12. Each detector 18 is provided for detecting 511 keV gamma radiation which does cross the tomographic field of view. Two groups of fiber optic cables 36 are connected at a proximal end to each detector 18, with the exception of a few detectors 18 to be described below which only have one fiber optic cable 36 connected thereto. The distal end of each fiber optic cable 36 is connected to an optical detector such as a photomultiplier tube (PMT) 38, as more clearly illustrated in FIG. 7.

Figure 7:
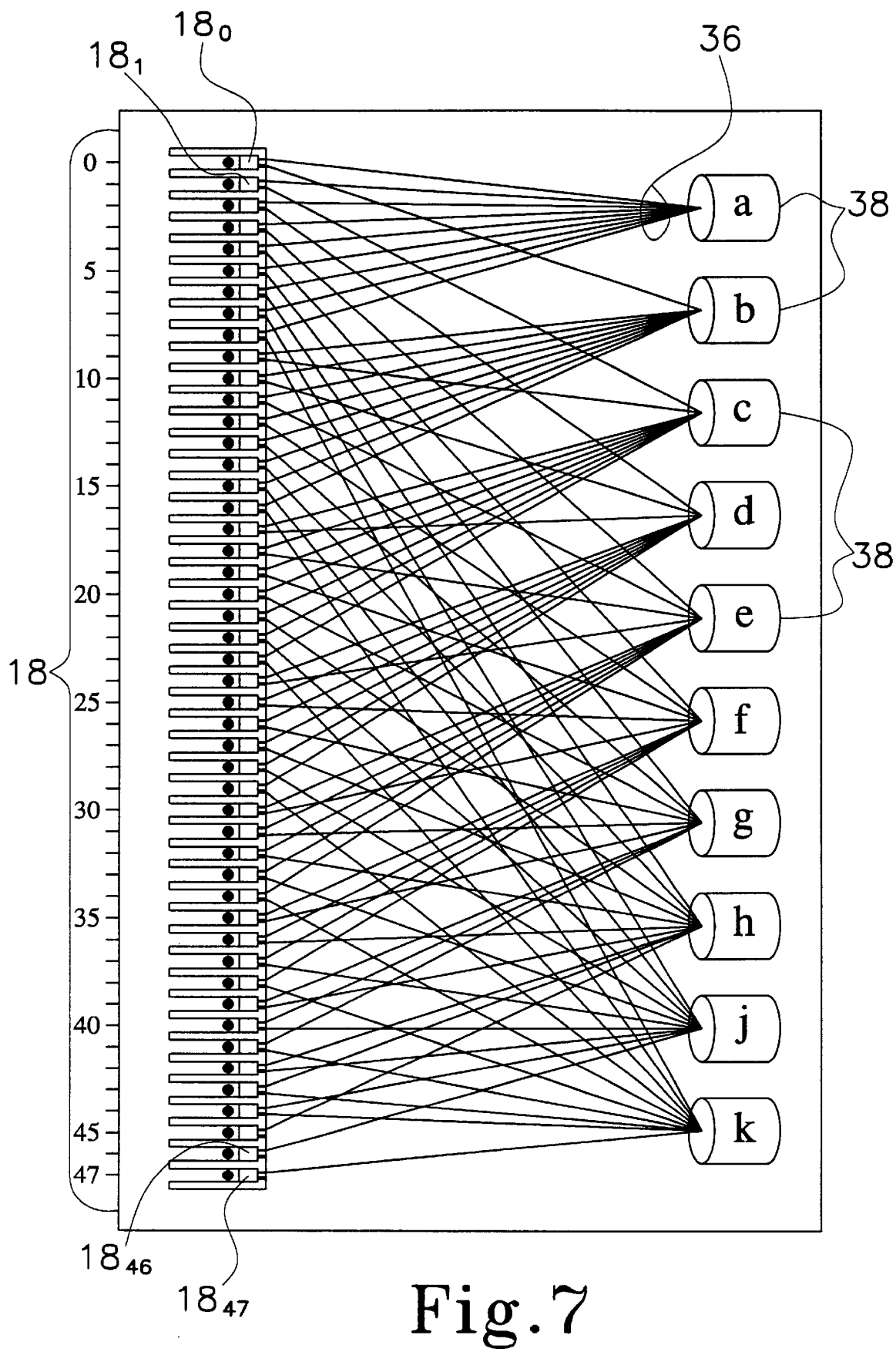
FIG. 7 is a schematic diagram representing a portion of the fiber optic connections between the dedicated gamma radiation detectors and the photomultiplier tubes.

Illustrated in FIG. 7 are 48 detectors $18_{0-47}$, interconnected to ten (10) PMT's $38a-k$. The fiber optic cables 36 interconnected between the detectors $18_{0-47}$ and the PMT's $38a-k$ are arranged such that no two fiber optic cables 36 are connected between the same detector 18 and the same PMT 38. Using the convention described above, Table 1 below more clearly illustrates the fiber optic connections.

TABLE 1

|   | b | c | d | e | f | g | h | j | k |
|---|---|---|---|---|---|---|---|---|---|
| a | 0 | 1 | 2 | 3 | 4 | 5 | 6 | 7 | 8 |
| b |   | 9 | 10 | 11 | 12 | 13 | 14 | 15 | 16 |
| c |   |   | 17 | 18 | 19 | 20 | 21 | 22 | 23 |
| d |   |   |   | 24 | 25 | 26 | 27 | 28 | 29 |
| e |   |   |   |   | 30 | 31 | 32 | 33 | 34 |
| f |   |   |   |   |   | 35 | 36 | 37 | 38 |

TABLE 1-continued

|   | b | c | d | e | f | g | h | j | k |
|---|---|---|---|---|---|---|---|---|---|
| g |   |   |   |   |   |   | 39 | 40 | 41 |
| h |   |   |   |   |   |   |    | 42 | 43 |
| j |   |   |   |   |   |   |    |    | 44 |
|   |   |   |   |   |   |   | 45 | 46 | 47 |

In this table, a through k are the PMT 38 labels and 0 through 47 are the detector 18 labels. It will be seen from the FIG. 7 and from the above table that PMT's 38a–g are optically coupled with nine (9) detectors 18 each while PMT's 38h, 38j and 38k are optically coupled with ten (10) detectors 18 each. Further, it will be seen that detectors $18_{0\text{-}44}$ are optically coupled with two (2) PMT's 38 each, while detectors $18_{45\text{-}47}$ are optically coupled with one (1) PMT 38 each. Of course, it will be understood that other configurations may be adopted as well and with similar results. Coincidence detection of pulse output from unique pairs of PMT's 38, or a single detection in PMT's 38h, 38j or 38k, determines which detector 18 received the near-side gamma radiation from its respective point source 12. The lengths of each optical fiber 36 in a fiber optic pair are equal in order to ensure that pulse output at the corresponding PMT's 38 is simultaneous.

From the foregoing description, it will be recognized by those skilled in the art that a coincidence transmission source offering advantages over the prior art has been provided. Specifically, the coincidence transmission source is provided for detecting coincident activity from a collimated point source. Moreover, the source of the present invention includes a detector dedicated to collecting attenuation data, thus changing the physical requirements of the attenuation detector as compared to an imaging detector and permitting it to be designed to achieve much lower dead time than a standard imaging detector. The collimated point source and dedicated detector are positioned with respect to the tomography device such the only a selected strip of the imaging detector is illuminated such that events unrelated to the attenuation are eliminated.

While a preferred embodiment has been shown and described, it will be understood that it is not intended to limit the disclosure, but rather it is intended to cover all modifications and alternate methods falling within the spirit and the scope of the invention as defined in the appended claims.

We claim:

1. A coincidence transmission source for accomplishing attenuation data collection relative to coincident activity from a radiation source associated with a tomography device having at least one imaging head, the imaging head having at least one imaging detector positioned to define a field of view and to collect emission data using a time coincidence method, said tomograph device defining a patient opening within the field of view, said coincidence transmission source comprising:

a radiation source positioned with respect to the tomograph device such that gamma radiation therefrom illuminates at least one imaging detector on the tomograph device; and an attenuation detector positioned outside the patient opening for acquiring attenuation data relative to said radiation source simultaneously with emission data collected by each imaging detector, said attenuation data being collected using a time coincidence method, said attenuation detector being independent from the at least one imaging detector and being fixed relative to and illuminated by said radiation source.

2. The coincidence transmission source of claim 1 wherein said radiation source includes at least one point source.

3. The coincidence transmission source of claim 1 further comprising a collimator positioned with respect to the tomography device such that a selected portion of the at least one imaging detector of the tomograph device is illuminated by said radiation source, thereby eliminating events unrelated to said attenuation data, said collimator defining an opening for exposing said radiation source to the selected portion of the at least one imaging detector of the tomograph device, said opening defining a top shield wall and a bottom shield wall, said top shield wall extending from said radiation source toward a far portion of the at least one imaging detector opposite said coincidence transmission source, said bottom shield wall extending toward a near portion of the at least one imaging detector opposite said coincidence transmission source, said opening further defining a pair of side shield walls spaced apart to limit a width of a collimated radiation beam emitted from said radiation source toward the selected portion of the at least one imaging detector.

4. The coincidence transmission source of claim 3 wherein said radiation source includes a plurality of point sources, thereby reducing activity requirements of each of said plurality of point sources.

5. The coincidence transmission source of claim 3 wherein said attenuation detector is disposed within said collimator behind said radiation source relative to the tomograph device imaging head.

6. The coincidence transmission source of claim 3 wherein said attenuation detector is disposed within said collimator and encapsulates said radiation source relative to the tomograph device imaging head, said attenuation detector being provided for detecting beta radiation emitted from said radiation source.

7. The coincidence transmission source of claim 1 wherein said attenuation detector is fabricated from a scintillation material which exhibits fast response times.

8. The coincidence transmission source of claim 7 wherein said attenuation detector is fabricated from Lutetium Oxyorthosilicate (LSO) coupled to a single photomultiplier.

9. The coincidence transmission source of claim 1 wherein said attenuation detector is selected to exhibit high sensitivity and low dead-time losses.

10. The coincidence transmission source of claim 1 wherein said coincidence transmission source is fixed relative to the imaging head of the tomograph device, said coincidence transmission source and the imaging head being rotated about a center of the tomograph device in order to obtain full coverage of the FOV of the tomograph device.

11. The coincidence transmission source of claim 1 adapted for use in a tomograph device having dual imaging heads, each imaging head having at least one imaging detector, said coincidence transmission source including two of said radiation source and two of said attenuation detector, with one each of said radiation source and said attenuation detector disposed across from each imaging bead such that a selected portion of the at least one imaging detector of the imaging head is illuminated thereby.

12. The coincidence transmission source of claim 1 adapted for use in a tomograph device including at least one imaging detector, said radiation source being movable within the tomograph device for collection of attenuation data relative to each of the at least one imaging detector.

13. The coincidence transmission source of claim 1 comprising a plurality of said attenuation detector, said coincidence transmission source further comprising a plurality of optical detectors, each of said plurality of attenuation detectors being optically coupled to at least one of said plurality of optical detectors, each of said plurality of optical detectors being optically coupled to a subset of said plurality of said attenuation detectors, said plurality of optical detectors being less than said plurality of attenuation detectors.

14. A coincidence transmission source for accomplishing attenuation data collection relative to coincident activity from a radiation source associated with a tomograph device having at least one imaging head, the imaging head having at least one imaging detector positioned to define a field of view and to collect emission data using a time coincidence method, said tomograph device defining a patient opening within the field of view, said coincidence transmission source comprising:

a radiation source positioned with respect to the tomograph device such that gamma radiation therefrom illuminates at least one imaging detector on the tomograph device;

a plurality of attenuation detectors positioned outside the patient opening for acquiring attenuation data relative to said radiation source simultaneously with emission data collected by each imaging detector, said attenuation data being collected using a time coincidence method, each of said plurality of attenuation detectors being selected and fabricated from a scintillation material which exhibits fast response times, high sensitivity and low dead-time losses, said plurality of attenuation detectors being independent from the at least one imaging detector and being fixed relative to and illuminated by said radiation source; and a plurality of optical detectors, each of said plurality of attenuation detectors being optically coupled to at least one of said plurality of optical detectors, each of said plurality of optical detectors being optically coupled to a subset of said plurality of said attenuation detectors, said plurality of optical detectors being less than said plurality of attenuation detectors.

15. The coincidence transmission source of claim 14 further comprising a collimator positioned with respect to the tomograph device such that a selected portion of the at least one imaging detector of the tomography device is illuminated by said radiation source, thereby eliminating events unrelated to said attenuation data, said collimator defining an opening for exposing said radiation source to the selected portion of the at least one imaging detector of the tomograph device, said opening defining a top shield wall and a bottom shield wall, said top shield wall extending from said radiation source toward a far portion of the at least one imaging detector opposite said coincidence transmission source, said bottom shield wall extending toward a near portion of the at least one imaging detector opposite said coincidence transmission source, said opening further defining a pair of side shield walls spaced apart to limit a width of a collimated radiation beam emitted from said radiation source toward the selected portion of the at least one imaging detector.

16. The coincidence transmission source of claim 15 wherein said attenuation detector is disposed within said collimator behind said radiation source relative to the tomograph device imaging head.

17. The coincidence transmission source of claim 15 wherein said attenuation detector is disposed within said collimator and encapsulates said radiation source relative to the tomograph device imaging head, said attenuation detector being provided for detecting beta radiation emitted from said radiation source.

18. The coincidence transmission source of claim 14 wherein said radiation source includes a plurality of point sources, thereby reducing activity requirements of each of said plurality of point sources.

19. A coincidence transmission source for accomplishing attenuation data collection relative to coincident activity from a radiation source associated with a tomograph device having at least one imaging head, the imaging head having at least one imaging detector for collecting emission data using a time coincidence method, the tomograph device defining a field of view, said tomograph device further defining a patient opening within the field of view, said coincidence transmission source comprising:

a collimator fixed relative to the imaging bead of the tomograph device, said coincidence transmission source and the imaging head being rotated about a center of the tomograph device in order to obtain full coverage of the field of view (FOV) of the tomograph device, said collimator defining an opening for exposing said radiation source to a selected portion of at least one imaging detector of the tomograph device, said opening defining a top shield wall and a bottom shield wall, said top shield wall extending from said radiation source toward a far portion of the at least one imaging detector opposite said coincidence transmission source, said bottom shield wall extending toward a near portion of the at least one imaging detector opposite said coincidence transmission source, said opening further defining a pair of side shield walls spaced apart to limit a width of a collimated radiation beam emitted from said radiation source toward the selected portion of the at least one imaging detector;

a radiation source disposed within said collimator, said collimator being positioned with respect to the tomograph device such that a selected portion of the at least one imaging detector of the tomograph device is illuminated, thereby eliminating events unrelated to said attenuation data; and an attenuation detector positioned outside the patient opening for acquiring attenuation data simultaneously with emission data collected by each imaging detector, said attenuation data being collected using a time coincidence method, said attenuation detector being disposed within said collimator behind said radiation source relative to the tomograph device imaging head, said attenuation detector consisting of a single crystal of dense, fast material, said attenuation detector being selected to exhibit low dead-time losses, said attenuation detector being independent from the at least one imaging detector and being fixed relative to and illuminated by said radiation source.

20. The coincidence transmission source of claim 19 wherein said radiation source includes a plurality of point sources, thereby reducing activity requirements of each of said plurality of point sources.

* * * * *